(12) United States Patent
Yoakum et al.

(10) Patent No.: US 9,763,962 B2
(45) Date of Patent: Sep. 19, 2017

(54) ESTRUS SYNCHRONIZATION PREPARATIONS AND EFFECTIVE CIDR-LESS PROTOCOLS

(71) Applicants: Jennifer Yoakum, Liberty City, TX (US); Hal Witt, Longview, TX (US)

(72) Inventors: Jennifer Yoakum, Liberty City, TX (US); Hal Witt, Longview, TX (US)

(*) Notice: Subject to any disclaimer, the term of this patent is extended or adjusted under 35 U.S.C. 154(b) by 0 days.

(21) Appl. No.: 14/090,450

(22) Filed: Nov. 26, 2013

(65) Prior Publication Data
US 2014/0194677 A1 Jul. 10, 2014

Related U.S. Application Data

(63) Continuation of application No. 13/203,020, filed as application No. PCT/US2010/000199 on Jan. 26, 2010, now abandoned.

(60) Provisional application No. 61/206,077, filed on Jan. 26, 2009.

(51) Int. Cl.
| | |
|---|---|
| *A61K 31/56* | (2006.01) |
| *A61K 31/57* | (2006.01) |
| *A61K 9/00* | (2006.01) |
| *A61K 31/565* | (2006.01) |
| *A61K 31/567* | (2006.01) |
| *A61K 31/573* | (2006.01) |
| *A61K 45/06* | (2006.01) |
| *A61K 47/10* | (2017.01) |
| *A61K 47/14* | (2017.01) |

(52) U.S. Cl.
CPC ............ *A61K 31/57* (2013.01); *A61K 9/0019* (2013.01); *A61K 31/565* (2013.01); *A61K 31/567* (2013.01); *A61K 31/573* (2013.01); *A61K 45/06* (2013.01); *A61K 47/10* (2013.01); *A61K 47/14* (2013.01)

(58) Field of Classification Search
CPC .. A61K 2300/00; A61K 31/565; A61K 31/57; A61K 31/567; A61K 31/573; A61K 45/06; A61K 47/10; A61K 47/14; A61K 9/0019
USPC ............................................ 514/170; 600/35
See application file for complete search history.

(56) References Cited

U.S. PATENT DOCUMENTS 5,589,457 A 12/1996 Wiltbank et al.

OTHER PUBLICATIONS

Samper et al, Current Therapy in Equine Reproduction, Elsevier, St. Louis, Mo; 2007.*
Azmi et al, Effects of a synthetic prostaglandin analogue, cloprostenol, on the corpus luteum of the guinea pig, Prostaglandins, 1982, pp. 519-526, vol. 24, No. 4.
Bradecamp, Current Therapy in Equine Reproduction—Chapter 3:Estrous Synchronization, 2007, Saunders Elsevier, St. Louis, MO, pp. 22-24.
DeJarnette, What's New in Estrus Synchronization?, Selections, 2002, pp. 7-10 downloaded on Mar. 4, 2010 from http://www.selectsires.com/selections/selections_fall2002.aspx.
International Search Report dated Mar. 17, 2010 in corresponding International Application No. PCT/US10/00199 filed Jan. 26, 2010, 3 pages.
Stoebel et al., Effect of Adrenocorticotropin and Cortisol on Luteinizing Hormone Surge and Estrous Behavior of Cows, Journal of Dairy Science, 1982, pp. 1016-1024, vol. 65, No. 6.
Abdullah et al, Comparison of oestrus synchronisation programmes in dairy cattle using oestradiol benzoate, short-acting progesterone and cloprostenol, or buserelin and cloprostenol, New Zealand Veterinary Journal, 2001, pp. 201-210, vol. 49, No. 5.

* cited by examiner

*Primary Examiner* — Jean Cornet
(74) *Attorney, Agent, or Firm* — Eric L. Sophir; Dentons US LLP (57) ABSTRACT

An injectable preparation of estrogenic and progestrogenic hormonal compounds in an anhydrous excipient injected to synchronize estrus in non-menstruating placental female animals, and a five to nine day protocol to apply the unique preparation to achieve estrus synchronization.

10 Claims, 5 Drawing Sheets

FIG. 1

(PRIOR ART)

FIG. 2

(PRIOR ART)

ESTRUS SYNCHRONIZATION PREPARATIONS AND EFFECTIVE CIDR-LESS PROTOCOLS

CROSS-REFERENCE TO RELATED APPLICATIONS

This application is a Continuation of U.S. application Ser. No. 13/203,020, filed 24 Aug. 2011, which is a National Stage Entry of International Application Ser. No. PCT/US2010/000199, filed 26 Jan. 2010 which claims priority from U.S. Provisional Application Ser. No. 61/206,077 filed on 26 Jan. 2009. Each of the above references is incorporated herein by reference in its entirety.

BACKGROUND OF THE INVENTION

A. Technical Field

The present invention generally relates to the fields of artificial insemination and embryo transfer in animals that undergo estrus and, more particularly, to the protocols and pharmaceuticals used to facilitate, manage, and control estrus synchronization in such animals.

B. Estrus Synchronization

In animal production, "estrus synchronization" traditionally refers to artificially synchronizing the estrous cycle throughout a group of female animals using hormone manipulation and supporting protocols. The animals may include such mammals as ruminants or non-menstruating placental females such as female cattle.

Cattle producers seek estrus synchronization in their herds because of its many economic benefits. First, estrus synchronization can reduce the number of days after a cow calves before she can begin a new pregnancy. This shortened interval increases the number of offspring a cow can produce in her lifetime. Second, and perhaps most importantly, because any particular breeding period is of limited duration (e.g., 45 to 90 days), and yet it may take 18 to 21 days to confirm a pregnancy after insemination, it is tremendously valuable to confirm pregnancy for as much of the herd as possible, as soon as possible, preferably with the first attempt at the start of the breeding period. If the entire herd can be estrus synchronized in the first week of the breeding period, then there is usually ample opportunity for a second and third opportunity to conceive during the remainder of the breeding period, while those who do not achieve estrus early will have fewer opportunities. Cows that do not conceive during the regular breeding period require additional interventions at the producer's expense. Third, cows that conceive early in the breeding season will produce calves that weigh more at weaning because the calves are older. Fourth, cows that calve early will have more days postpartum before the beginning of the next breeding season, which serves to improve the cow's overall health. Fifth, estrus synchronization also allows the producer to synchronize the feed, supplements, immunizations, and treatments for all the cows in the herd, which allows for more efficient management and greater opportunities for profit. Additionally, estrus synchronization allows producers to breed virgin heifers three weeks before inseminating the main herd, which gives the heifers additional recovery time after their first calving before the next breeding season begins.

For these and other benefits, producers attempt to coordinate the onset of estrus in their animals, which, without intervention, is typically asynchronous across a group of animals. To achieve a synchronized onset of estrus, producers use hormones and supporting protocols to intervene in their animals' estrous cycles.

C. Estrous Cycle

The estrous cycle comprises recurring physiologic changes that are induced by mammalian reproductive hormones. The mammalian reproductive system includes the hypothalamic system which releases gonadotropin releasing hormone (GnRH), as well as the pituitary system that secretes follicle stimulating hormone (FSH) and luteinizing hormone (LH). The mammalian ovaries release hormones that include estrogens and progesterone. Species that have estrous cycles characterized by non menstruating placental females reabsorb the endometrium if fertilization and conception does not occur during that particular cycle. In such species, females are generally only sexually active during the estrus phase of their cycle, a condition commonly referred to as being "in heat." Therefore, an animal may be described as "in estrus" when it is in that particular part of "the estrous cycle."

There are four basic phases to the estrous cycle in mammals and, therefore, in all female cattle (including genus *Bos* of the taurine and *zebu* species), ewes, does, cows, nannies, mares, and female ruminants. In the initial phase, the proestrus phase, one or more follicles of the ovary begin to grow. Typically this phase can be as short as one day, or as long as three weeks, depending upon the mammalian species. Under the natural influence of estrogen, the lining of the uterus (the endometrium) develops. The second phase is estrus proper and refers to the days when the animal is "in heat." In this phase, under regulation by gonadotropic hormones, ovarian follicles mature and estrogen secretions begin to influence the reproductive system. In female cattle, ovulation may occur spontaneously during this phase. Estrus may continue for a number of days, followed by interestrus. During the third phase, metestrus, the indications of estrogen stimulation diminish and the corpus luteum begins to form. The corpus luteum is essential for establishing and maintaining a pregnancy. The corpus luteum produces progesterone which: (a) prepares the uterus for pregnancy by thickening and developing the endometrium, (b) maintains the pregnancy if fertilization occurs, and (c) inhibits the cattle from showing signs of standing estrus and ovulating. Generally, the larger the corpus luteum the more progesterone it produces, and in the presence of progesterone, the dominant follicle will not rupture, meaning no ovulation occurs. Further, the corpus luteum secretions inhibit LH and FSH. Also, the uterine lining begins to secrete progesterone. This third phase is generally short and may last one to five days. The final stage of the estrous cycle is diestrus, which is characterized by the production of progesterone by the corpus luteum. In the absence of a pregnancy, the diestrus phase terminates with the regression of the corpus luteum. The lining in the uterus is not shed (as in menstruating mammalian species) but is reconfigured for the next cycle.

D. Current Techniques for Estrus Synchronization

Today, beyond true synchronization of estrus among a herd, estrus synchronization also encompasses a wide variety of hormonal manipulation techniques that attempt to control the date(s) on which a particular female can either be successfully inseminated or otherwise impregnated. One of the most reliable synchronization techniques uses a controlled intravaginal drug release (CIDR®) device that is inserted vaginally and left in place to introduce hormones into the animal. CIDR® devices are marketed under the CIDR® trademark by InterAg of Hamilton, New Zealand, although we use the term in our descriptions to refer generically to such vaginal inserts.

Figure 1:
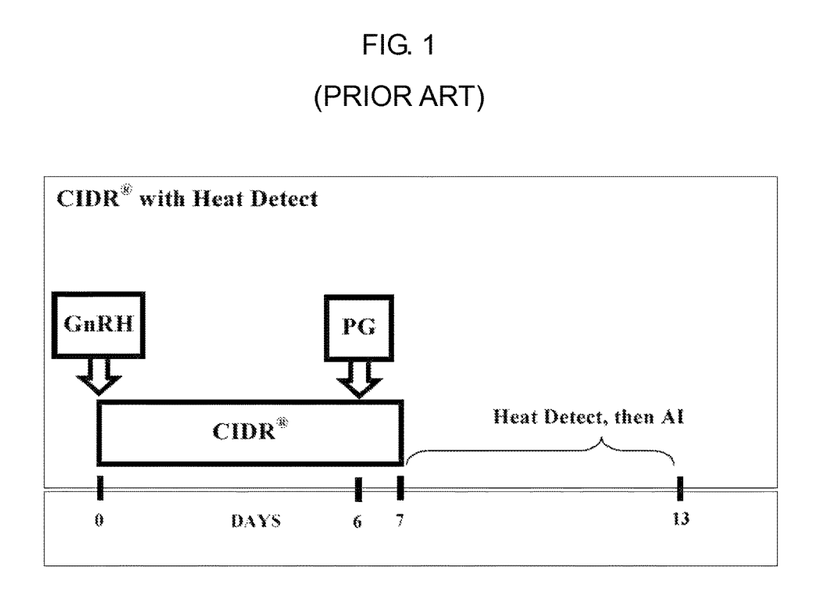
FIG. 1 (Prior Art) depicts a CIDR® protocol that requires heat detection before artificial insemination (AI).
Figure 2:
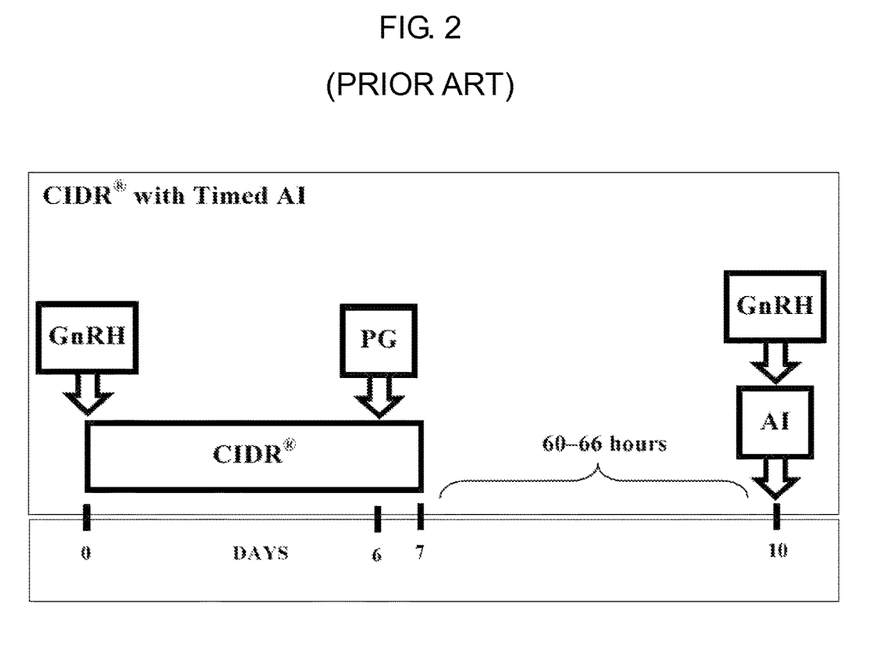
FIG. 2 (Prior Art) depicts a CIDR® protocol with timed artificial insemination (TAI) not dependent upon detection of estrus.

FIGS. 1 and 2 show two typical protocols for using the CIDR® product. There are many different protocols that require a CIDR® product; the two examples shown in FIGS. 1 and 2 are not an exhaustive list. FIG. 1 (Prior Art) depicts a CIDR® protocol that requires heat detection before artificial insemination (AI). FIG. 2 (Prior Art) depicts a CIDR® protocol with timed artificial insemination (TAI) not dependent upon detection of estrus.

CIDR® cattle inserts typically contain 1.38 grams of progesterone in elastic rubber molded over a nylon spine. The devices are typically packaged in a plastic pouch and are inserted using a special applicator device. CIDR® cattle inserts are administered intravaginally, one per animal, in beef cows and heifers. The CIDR® cattle insert releases progesterone during a seven day treatment period. CIDRs® typically allow for sustained release of hormones to delay estrus for five to fourteen days while the cow's corpus luteum is hopefully held intact to allow proper development of the cow's follicles until full estrus is allowed to proceed, often under the influence of a prostaglandin injection.

Recommended administration, in order to assure satisfactory synchronization, includes an injection of Lutalyse® sterile solution (dinoprost tromethamine) that is typically given to all synchronized cattle either at the time of, or within one day before, CIDR® removal. Removal of the insert on treatment Day Six or Seven results in a drop in plasma progesterone, ideally triggering estrus within three days.

Referring again to FIG. 1 (Prior Art), the use of a CIDR® insert is shown to extend from Day Zero to Day Seven of the protocol. Associated with placement of the insert on Day Zero is the administration of an injectable gonadotropin releasing hormone (GnRH). On Day Six or Seven, with removal of the CIDR® insert, prostaglandin (such as Lutalyse®) is typically administered by injection. In the protocol shown in FIG. 1, the user must investigate and detect symptoms of heat in the animal, and thereafter, carry out the artificial insemination (AI) process. This heat detection and AI process typically occurs between Day Seven and Day Thirteen as calculated from Day Zero, the day of the placement of the CIDR® device.

FIG. 2 (Prior Art) depicts another CIDR® protocol that is similar in most respects to the protocol described in FIG. 1. However, rather than rely upon the detection of heat in the animal, this second protocol calls for a time period of 60-66 hours after Day Seven (and the removal of the CIDR® insert) for a further administration of a dose of GnRH and subsequent AI. As indicated in FIG. 2, this typically results in a Day Ten artificial insemination of the animal.

Besides CIDR®-based synchronization protocols, there are also "CIDR®-less" synchronization protocols—meaning methods that do not require the use of a CIDR® or any intravaginal device to administer hormones.

E. Problems with Existing Protocols

To date, many different hormonal preparations and related protocols are well known to those of ordinary skill in the art. However, the success rates associated with the prior art—with or without a CIDR®—remain less than desirable, typically allowing for successful implantation or insemination in fewer than half of the attempts.

Additionally, various problems are known to exist with the use of the CIDR® insert. Although CIDR® promoters assert much better results, it is not unusual to experience conception rates as low as 20% with many CIDR® protocols, and even lower rates with virgin heifers. Moreover, results are diminished by high rates of infection and vaginitis, as well as animal discomfort and stress that are fairly common with CIDR® inserts. Use of the CIDR® insert requires careful cleaning of the vulva to avoid infection, and many protocols still require the detection of heat for effective AI. It would be desirable, therefore, to establish a reliable estrus synchronization protocol that does not require the use of a CIDR® insert.

SUMMARY OF THE INVENTION

The present invention includes both unique preparations and protocols that, among other benefits, (1) dramatically improve estrus synchronization rates in healthy, mature, cycling female cattle as well as in virgin heifers, (2) help preserve the corpus luteum, (3) improve the success rate of embryo transfer (transplantation), and (4) enable CIDR®-less estrus synchronization, thereby avoiding the infections, vaginitis, and animal discomfort that occur with CIDR devices.

The present invention is embodied in an injectable preparation for promoting CIDR-less estrus synchronization in non-menstruating placental females, which includes: (a) a steroidal estrogenic compound such as estradiol 17-β (E2), estradiol benzoate, or the like in an amount effective to induce estrus in healthy, mature, cycling female cattle; and (b) a steroidal progestin such as progesterone, hydroxyprogesterone, medroxyprogesterone, altrenogest, norgestomet, levonorgestrel, or other progestogenic compound or any derivatives, analogs, or agonists thereof, and any combinations thereof, for preserving the corpus luteum intact for a period of at least five days after its injection; and (c) an excipient compounded with an estrogenic compound and a progestin to produce an injectable compound.

One embodiment of the preparation is made where the estrogenic compound, the progestin, and the excipient are combined in quantities such that the estrogenic compound is in concentrations from 0.05% to 1.0% by volume relative to the overall injectable preparation, preferably from 0.06 to 0.125%, and the combination is in a form suitable for intramuscular delivery.

Another embodiment of the present invention includes a preparation which, when compounded, obtains progestogenic concentrations of at least 30 mg/mL.

The present invention is also embodied in protocols for improving estrus synchronization and fertilization rates in non-menstruating female animals without utilizing an intravaginal hormone dispensing device. The protocols are based on four ordered steps: (1) injecting intramuscularly one or more healthy, cycling females with a first steroidal hormone preparation to prepare such females to induce estrus; (2) administering a second preparation principally prostaglandin, or its biologically functional, to actually initiate estrus; (3) administering a third preparation of an estrogenic compound to synchronize estrus; and (4) impregnating each female animal, either through artificial insemination or otherwise.

The first preparation is administered by intramuscular injection within the first twelve hours of Day Zero. The second preparation is administered by intramuscular injection no sooner than the beginning of Day Five but no later than the end of Day Eight. The third preparation is administered about one day after the second preparation, and the animals are artificially inseminated or naturally bred about one day after the administration of the third preparation.

The first step is to administer to each female animal by intramuscular injection approximately 2 cm3 of a first steroidal hormone preparation combining an estrogenic compound with a progestin. Next, 5 to 8, preferably 6 or 7, and ideally 6 days later, each female receives an intramuscular injection of a second preparation, namely prostaglandin, or its biologically functional equivalent, in an amount to initiate estrus and ovulation. The final step in the typical process is the further step of impregnating the female animals, preferably through artificial insemination. The two injections properly administered, combined with a subsequent estradiol injection, improve estrus synchronization rates, increase conception rates in virgin heifers, and achieve synchronization without the need for a CIDR®, which omission reduces the risk of vaginitis and vaginal infections and decreases animal discomfort.

A related preparation and protocol is involved in an alternative embodiment that is used to synchronize donor cows. Such embodiments include a base protocol the DonorSync™ Protocol, to use the preparation of the foregoing embodiments to prepare donor cows for embryo transfer (ET). In ET practice, donor cows are often treated with a hormone protocol to facilitate embryo production. The donor cow is inseminated at the appropriate time, and the embryos are collected about 6-8 days after breeding. When the donor cow's embryos are collected, they need to be immediately transplanted into recipient cows. For the embryo to survive and become a live pregnancy, each recipient cow's estrous cycle must be in the same state as the donor cow's cycle so that the recipient cow's uterus is prepared to receive the embryo. The present invention protocol, using DonorSync™, with its higher concentration of progestin than in the SuperSync™ preparation, has been shown to be highly affective in resetting the follicular wave. When followed by an FSH and PG protocol, the DonorSync™ yields excellent results in producing transferable embryos.

Further, the present invention's protocols and preparations are also used in ET using frozen embryos.

It will also be appreciated that many invaluable aspects of the present invention could also be understood or expressed from other vantage points. From the context of a kit, for example, it can be appreciated that aspects of the present invention allow for a kit that contains both preparations and protocols to be followed to achieve estrus synchronization. Still other embodiments of the invention relate to products made by the described protocols as well as apparatuses and systems for performing all or part of such protocols.

Many other objects, features, and advantages of the present invention will be evident from the remainder of this application in light of a more exhaustive understanding of the numerous difficulties and challenges faced by the prior art, which in turn will be evident to those skilled in the art. In the end, while there are many alternative variations, modifications, and substitutions within the scope of the invention, one of ordinary skill in the art should consider the scope of the invention from a review of the claims appended hereto (including any amendments made to those claims in the course of prosecuting this and related applications) as considered in the context of the prior art and the various descriptions of this application.

BRIEF DESCRIPTION OF THE DRAWINGS

The accompanying drawings constitute a part of this specification and illustrate embodiments of the invention. The present disclosure can be better understood by referring to the following figures. The components in the figures are not necessarily to scale, emphasis instead being placed upon illustrating the principles of the disclosure.

DETAILED DESCRIPTION OF PREFERRED EMBODIMENTS

The teachings of the present inventions are preferably embodied as injectable hormonal preparations and as protocols that use such preparations in order to improve estrus synchronization and achieve a much higher percentage of estrus synchronization as well as the desired preservation of larger corpus luteum sizes. It will be understood by those skilled in the art that the protocols and administered preparations described below in conjunction with the present invention are further facilitated by other techniques known to optimize the benefits of estrus synchronization. These other techniques include the maintenance of adequate nutrition as well as efforts to maintain sufficient overall body scores for the cows and heifers. Those skilled in the art will also recognize alternative applications of the compounds and methods of the present invention that may include the preparation of recipient cows for implantation of embryos.

For reference in various aspects of the preferred embodiments of the present invention, Applicant has developed a preferred formulation for a steroidal hormonal preparation that Applicant expects to commercialize under the designation "SuperSync™." The formulation of the SuperSync™ preparation is a combination of an estrogenic compound, a progestin, and appropriate excipients to achieve an injectable form. By an "estrogenic" compound, we mean an artificial or synthetic estrogen (i.e., a steroidal estrogenic compound) or derivatives, analogs, or agonists thereof, and any combinations thereof. Likewise, by a "progestin," we mean an artificial or synthetic progesterone (i.e., a steroidal progestogenic compound), such as, for example, progesterone, hydroxyprogesterone, medroxyprogesterone, altrenogest, norgestomet, levonorgestrel, or other progestogenic compound, or derivatives, analogs, or agonists thereof, and any combinations thereof. Preferably, the estrogenic compound is selected from the group of estradiol 17-β or estradiol benzoate, or their derivatives, analogs, agonists and the like.

To achieve a preparation that is suitable for intramuscular injection, the estrogenic compound and the progestin are compounded with an excipient that preferably combines an anhydrous carrier base (such as sesame seed oil, cotton seed oil, olive oil) with one or more excipient solvents. In the preferred embodiments, the excipient solvents are phenylmethanol (approximately 10% of the final volume) and a co-solvent benzoic acid phenylmethyl ester (approximately 10% of the final volume). The excimer is compounded with at least 1 mg/mL estrogenic compound (preferably 1.25 mg/mL). For a 2 cm3 dose, preferred preparations provide from 2 to 3 mg estradiol 17-β, which is an amount effective to initiate estrus or, in other words, to reset the follicular wave in a heifer or a cow (including a non-bovine cow), and at least 30 mg/mL progestogenic compound (preferably more than 40 mg/mL and approximately 60 mg/mL), which has been found to be effective at preserving the corpus luteum intact for five or more days from the date of injection. The maximum amount of estradiol 17-β should not ever exceed 5 mg per dose.

Figure 3:
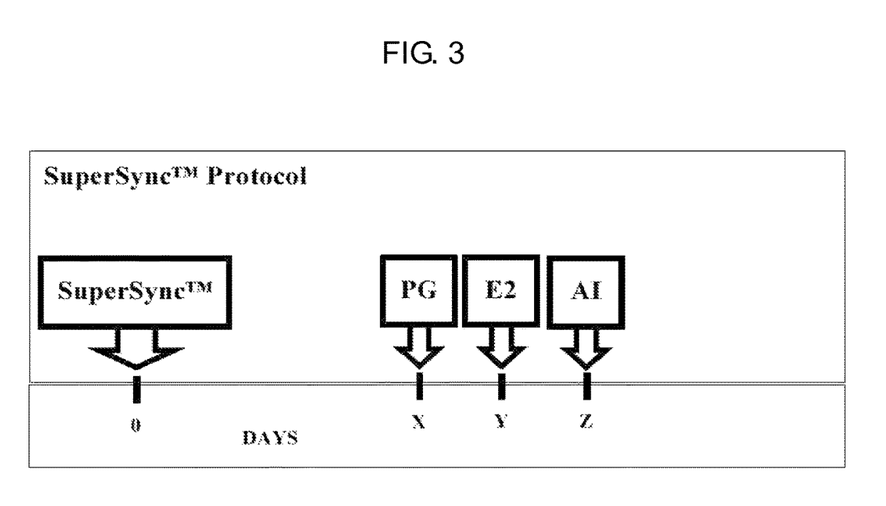
FIG. 3 depicts a depicts the methodology of a SuperSync™ Protocol according to the processes of the present invention.
Figure 4:
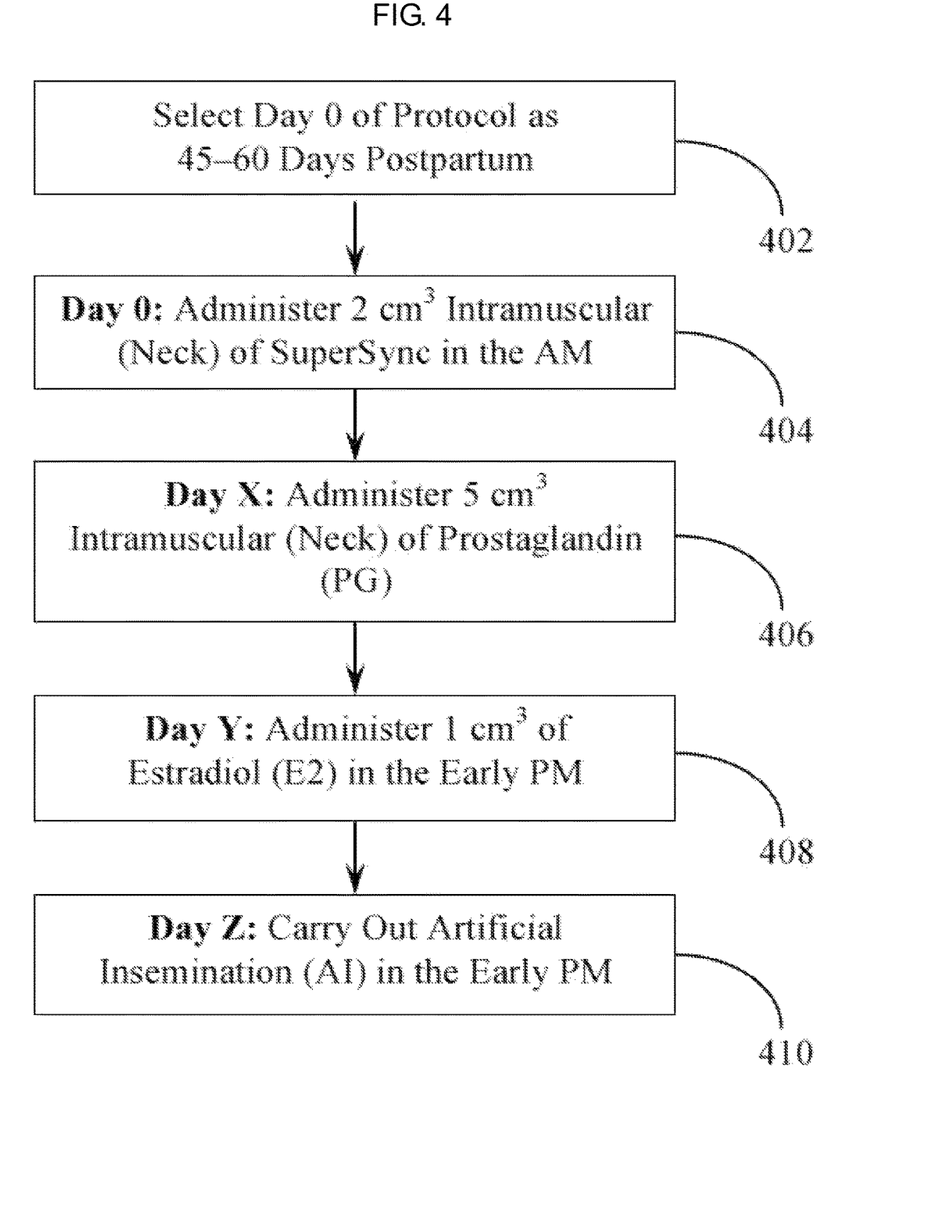
FIG. 4 provides a flow chart describing in a step-by-step manner the methodology of the protocol of the present invention.

FIG. 3 depicts the methodology of a SuperSync™ Protocol according to the processes of the present invention. FIG. 4 provides a flow chart describing in a step-by-step manner the methodology of the protocol of the present invention. Initially (Step 402 in FIG. 4), it is necessary to identify a Day Zero for the protocol by determining a time period of 45-60 days postpartum. Starting the protocol no earlier than this time period ensures an involuted uterus. On Day Zero (Step 404), 2 cm3 of the proprietary formulation (SuperSync™) is administered by intramuscular (IM) injection, preferably in the neck of the animal. The formulation of the proprietary preparation may vary moderately, but in the preferred embodiment includes progesterone and estradiol in a ratio of 60 mg/mL progesterone to 1.25 mg/mL estradiol. This proprietary preparation should be administered in the first twelve hours of Day Zero.

The administered preparations described above in the protocol (SuperSync™ Protocol) generally carry out the following functions in the process of estrus synchronization. The proprietary preparation of progestin and estradiol provides a unique simultaneous combination of effects. As indicated above, the progestin component keeps a cow or heifer out of heat and extends the estrous cycle. The progestin/estradiol combination, when administered at Day Zero, resets the follicular wave in the animal. The prostaglandin (PG) prepares for initiation of heat in the animal. Estradiol, administered subsequent to prostaglandin, further facilitates ovulation. Gonadotropin releasing hormone (GnRH), as indicated above, is a hormone that triggers ovulation or starts development of a new follicular wave. Lutenizing hormone (LH) also triggers ovulation and follicle stimulating hormone (FSH) promotes follicular formation. Progestin mimics natural progesterone produced by the corpus luteum after ovulation which prepares the uterus for pregnancy and serves to keep the cow or heifer from coming back into heat.

Estradiol is the most common, and generally considered to be the most effective estrogen hormone. Estradiol 17-β is a naturally occurring hormone that tends to result in the quickest reaction in cows. Estradiol benzoate is a possible alternative to estradiol 17-β. The compositions contained in the proprietary preparation (SuperSync™) administered on Day Zero, therefore, carry out the important functions towards the goals of the protocol. The progestin helps to preserve the corpus luteum in good condition by shutting down the pituitary function. In essence the progestin ensures that the corpus luteum remains intact. The estradiol functions to reset the follicular wave. Specifically, estradiol 17-β (E2) knocks off the dominant follicle, thereby releasing the ovacyte (ovulation), which becomes the egg (once fertilized). The ruptured follicle also either becomes the corpus luteum or adds to it (presuming that a corpus luteum was pre-existing).

The second action step of the SuperSync™ Protocol (Step 406) takes place on Day X, where Day X is any day from 5 to 8 days after Day Zero, although it may start as soon as the corpus luteum has adequately redeveloped. On Day X, therefore, 5 cm3 of prostaglandin (PG) is administered by intramuscular injection, preferably in the neck of the animal, and preferably within four hours of 8:00 am and optimally within one hour of 9:00 am. In the preferred embodiments, the prostaglandin (PG) utilized may be a product marketed as Lutalyse® (a Registered Trademark of Pharmacia & Upjohn Co. of Michigan) which contains the naturally occurring prostaglandin F2α (dinoprost) as the tromethamine salt. Each milliliter contains dinoprost tromethamine equivalent to 5 mg dinoprost. Alternately, in the preferred embodiments, the prostaglandin (PG) may be a product marketed as Estrumate® (a Registered Trademark of Schering-Plough of New Jersey) which is a synthetic prostaglandin analogue structurally related to prostaglandin F2α. Each milliliter of the colorless, aqueous solution contains 263 mcg of cloprostenol sodium (equivalent to 250 mcg of cloprostenol). In any case, the prostaglandin functions to put a heifer or cow into heat, thereby disrupting the yellow tissue that makes up the corpus luteum, causing the release of scent and other signs of heat. This process thereby forces ovulation which is the start of complete estrus.

The third action step (Step 408) typically occurs on Day Y, which is the day immediately following Day X, but should occur within 12 to 36 hours after administering the second preparation wherein 1 cm3 of estradiol is administered, sometime on Day Y, preferably within four hours of 1:00 pm, and optimally within one hour of 1:00 pm. This administration of estradiol functions to stimulate the pituitary to release hormones causing ovulation (i.e., ovacyte to drop, vulva to swell, etc.). The estradiol used here and elsewhere in the preferred protocols is preferably estradiol 17-β (E2) or estradiol benzoate, although it should be appreciated that various other natural or synthetic estrogenic compounds, or their derivatives, analogs, or agonists, and any combinations thereof, may be used as less preferred alternatives. It will also be appreciated that, at the risk of marginalizing the benefits of the dosing in the preferred embodiments, alternate concentrations and/or volumes may also be used. For instance, it is appreciated that certain aspects of the invention can be accomplished through administration of other concentrations of the estrogen compound, so long as at least one milligram of estradiol 17-β, or the biologically functional equivalent dose of an alternate steroidal estrogenic compound, is administered.

The final action step (Step 410) in the SuperSync™ Protocol is carried out on Day Z, which is the day immediately following Day Y, wherein insemination is effected on Day Z, preferably within four hours of 2:00 pm, and optimally within one hour of 2:00 pm. Insemination may be carried out with frozen or thawed semen, with actual fertilization typically occurring 4-6 hours after insemination.

Those skilled in the art will recognize that the protocol of the present invention as described above is less labor intensive than those protocols associated with the use of the CIDR® device and may be used on female animals that are genetically ill-suited to CIDR® use (e.g., Beefmaster cows that typically cannot retain a CIDR® in place) or individual females that do not tolerate the CIDR® (e.g., vaginal scarring from previous pregnancies). The present invention's protocol is less traumatic for the cows and heifers, and may be expected to generally maintain better overall health during administration of the protocol than with the CIDR® system. Although the protocol and the proprietary preparation have been described in conjunction with a set of preferred embodiments, it will be recognized by those of ordinary skill in the art that certain modifications to the protocols and to the formulation may be made without departing from the spirit and scope of the invention. Variations based on the size of the herd and/or the size and overall health of the individual cows and heifers, will become apparent. Likewise, variations on the ratio of the compounds making up the proprietary preparation will be apparent to those skilled in the art upon a consideration of the specific applications to which the protocol is directed. In other words, some such variations would be appropriate for use of the protocols in conjunction with natural or artificial insemination versus a similar use of the protocols for embryo implantation. As indicated, these variations, given the basic concepts of the present invention, do not necessarily depart from the spirit and scope of the invention.

The results that Applicants are able to achieve using the present invention are surprisingly better than the prior art. For instance, although still unpublished, controlled studies have indicated dramatically greater conception rates in virgin dairy Holstein heifers using a CIDR®-less protocol where the second preparation was administered on Day 6. Similarly, although results may vary with poor controls, estrus synchronization using the present invention has been preliminarily reported to such a degree that more then 90% of a herd reached estrus almost simultaneously, reportedly with two hours of each other.

Many other objects, features, and advantages of the present invention will be evident from the remainder of this application in light of a more exhaustive understanding of the numerous difficulties and challenges faced by the prior art, which in turn will be evident to those skilled in the art. In the end, while there are many alternative variations, modifications, and substitutions within the scope of the invention, one of ordinary skill in the art should consider the scope of the invention from a review of the claims appended hereto (including any amendments made to those claims in the course of prosecuting this and related applications) as considered in the context of the prior art and the various descriptions of this application.

Figure 5:
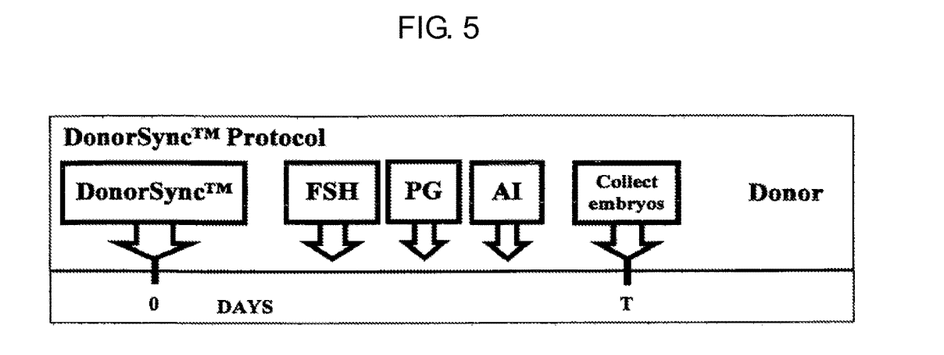
FIG. 5 depicts the methodology of a DonorSync™ Protocol according to the processes of the present invention.

For instance, an alternative embodiment of the present invention involves use of a form of the first preparation (and in a higher dose) in donor cows to achieve successful estrus synchronization in preparation for embryo production, collection, and transfer into recipient cows. This embodiment is effective in taurine cows but is especially effective in Brahman or other *zebu* cows. FIG. 5 depicts the methodology of a DonorSync™ Protocol according to the processes of the present invention. For this embodiment, one or more of the preferred variations of the Day Zero preparation from the previous embodiments is used to prepare the donor cow. The injected amount of such preparations, however, is increased—preferably from 30% to 150% more than in the prior description. Most preferably, the donor cow is injected with the first preparation in a dose of from 3.0 to 4.5 cm3 and, beginning four days later, a multi-day course of follicle-stimulating hormone (FSH) administered intramuscularly twice daily to produce more ovacytes, concluding with injections of prostaglandin to rupture all of the developed follicles. After ovulation, the donor cow is inseminated, usually several times in over a 12 to 24 hour period. Thereafter, on Day T, typically Day 7, the embryos are collected from the donors and transferred either to the recipients or preserved by freezing.

What is claimed is:

1. A method for improving estrus synchronization in a plurality of cycling; female cows, the method comprising:
   (a) administering on Day Zero to a plurality of cycling, female cows by intramuscular injection a first steroidal hormone composition comprising 2-5 mg of estradiol 17-β, 60-120 mg of a progestogen compound, and an anhydrous excipient, wherein Day Zero is at least 45 days postpartum;
   (b) administering on Day X to the plurality of cycling female cows a second composition comprising dinoprost or cloprostenol in an amount effective to initiate estrus, wherein Day X is from 5 to 6 days 7 after Day Zero; and
   (c) administering on Day Y to the plurality of cycling female cows a third composition comprising 2-5 mg of estradiol 17-β in an amount effective to synchronize estrus, wherein Day Y is from 12 to 36 hours after administration of the second composition;
   wherein
   the plurality of cycling female cows do not comprise a controlled intravaginal hormone release device; and
   on a date during estrus proper, an increased number of the plurality of cycling female cows are in heat and can be impregnated compared to cows using a controlled intravaginal hormone release device.

2. The method of claim 1, further comprising the additional step of attempting to impregnate a plurality of cycling female cows on Day Z, wherein Day Z is not less than twelve hours after administration of the third composition.

3. The method of claim 2, wherein:
   the first composition is administered within the first twelve hours on Day Zero;
   the second composition is administered within four hours of 8:00 AM on Day X where Day X is 6 days after Day Zero;
   the third composition is administered within four hours of 1:00 PM on Day Y; and
   the attempting to impregnate comprises artificial insemination within four hours of 2:00 PM on Day Z.

4. The method of claim 3, wherein:
   the first composition is administered within the first twelve hours on Day Zero;
   the second composition is administered within one hour of 9:00 AM on Day X where Day X is 6 days after Day Zero;
   the third composition is administered within one hour of 1:00 PM on Day Y; and
   the insemination is performed within one hour of 2:00 PM on Day Z.

5. The method of claim 1, wherein the progestogen compound of the first steroidal hormone composition is a progestin.

6. The method of claim 5, wherein the progestogen compound of the first steroidal hormone composition is selected from the group consisting of progesterone, hydroxyprogesterone, medroxyprogesterone, altrenogest, norgestomet, and levonorgestrel, or agonist or mixture thereof.

7. The method of claim 1, wherein the estradiol 17-β is present in the first steroidal hormone composition at a concentration of:
   (a) at least 0.025% by volume;
   (b) about 0.05% to about 1.0% by volume; or
   (c) about 0.06% to about 0.125% by volume.

8. The method of claim 1, wherein the plurality of cycling female cows are virgin heifers.

9. The method of claim 1, wherein Day X is 6 days after Day Zero.

10. The method of claim 1, wherein more than 90% of the plurality of cycling female cows are in heat during estrus proper.

\* \* \* \* \*